(12) United States Patent
Iwasaki

(10) Patent No.: US 7,626,165 B2
(45) Date of Patent: Dec. 1, 2009

(54) FOCUSED ION BEAM APPARATUS AND METHOD OF PREPARING/OBSERVING SAMPLE

(75) Inventor: Kouji Iwasaki, Chiba (JP)

(73) Assignee: SII Nano Technology Inc., Chiba (JP)

( * ) Notice: Subject to any disclaimer, the term of this patent is extended or adjusted under 35 U.S.C. 154(b) by 174 days.

(21) Appl. No.: 11/703,292

(22) Filed: Feb. 7, 2007

(65) Prior Publication Data
US 2008/0073586 A1    Mar. 27, 2008

(30) Foreign Application Priority Data
Feb. 14, 2006    (JP) .............................. 2006-036605

(51) Int. Cl.
*H01J 37/26* (2006.01)
*G01N 13/10* (2006.01)
*G01N 23/22* (2006.01)

(52) U.S. Cl. ................. 250/310; 250/492.1; 250/492.2; 250/492.21; 430/297

(58) Field of Classification Search .............. 250/491.1, 250/492.1, 492.2, 492.21, 492.23, 492.3, 250/306, 307, 309, 310, 311, 492.22; 430/296, 430/297, 298, 299
See application file for complete search history.

(56) References Cited

U.S. PATENT DOCUMENTS

| | | | |
|---|---|---|---|
| 4,588,890 A * | 5/1986 | Finnes .......................... 250/307 |
| 5,986,264 A * | 11/1999 | Grunewald ................... 250/310 |
| 6,920,685 B2 | 7/2005 | Oike | |
| 7,094,312 B2 * | 8/2006 | Libby et al. ............. 156/345.39 |
| 2003/0071214 A1 * | 4/2003 | Shimoma et al. ............ 250/310 |
| 2004/0031936 A1 * | 2/2004 | Oi et al. ................... 250/492.23 |
| 2005/0184237 A1 * | 8/2005 | Takane et al. ................ 250/311 |
| 2005/0236587 A1 * | 10/2005 | Kodama et al. ......... 250/492.21 |
| 2006/0065854 A1 * | 3/2006 | Shichi et al. ............ 250/492.21 |
| 2006/0091321 A1 * | 5/2006 | Kaga et al. ................ 250/491.1 |
| 2006/0231752 A1 * | 10/2006 | Houge et al. ................. 250/306 |
| 2008/0067385 A1 * | 3/2008 | Tokuda et al. ................ 250/310 |

FOREIGN PATENT DOCUMENTS

| JP | 2973211 | 7/1991 |
|---|---|---|
| JP | 2935180 | 5/1998 |
| JP | 2002-367115 | 12/2002 |

* cited by examiner

*Primary Examiner*—Jack I Berman
*Assistant Examiner*—Nicole Ippolito Rausch
(74) *Attorney, Agent, or Firm*—Brinks Hofer Gilson & Lione

(57) ABSTRACT

A focused ion beam apparatus includes a sample base for mounting a sample, a three axis stage capable of moving the sample base in three directions: along two axes on a horizontal face and a vertical axis, and a first focused ion beam barrel and a second focused ion beam barrel for irradiating the sample with focused ion beams, the first focused ion beam barrel and the second focused ion beam barrel being arranged such that directions of the focused ion beams are substantially opposed to each other in a plane view thereof and are inclined in substantial line symmetry with regard to the vertical axis in a side view thereof.

14 Claims, 7 Drawing Sheets

FOCUSED ION BEAM APPARATUS AND METHOD OF PREPARING/OBSERVING SAMPLE

This application claims priority under 35 U.S.C. §119 to Japanese Patent Application No. JP2006-036605 filed Feb. 14, 2006, the entire content of which is hereby incorporated by reference.

BACKGROUND OF THE INVENTION

The present invention relates to a focused ion beam apparatus for preparing a sample by irradiating the sample with a focused ion beam from a focused ion beam barrel, and a method of preparing/observing a cross section of a sample.

In the background art, in steps of fabricating a semiconductor device or a thin film magnetic head with a laminated layer structure, a focused ion beam apparatus is utilized as a method of evaluating the fabricating steps. For example, by irradiating a predetermined position of a sample with a focused ion beam from a focused ion beam apparatus to carry out etching, a cross section for observation is fabricated. Further, the cross section for observation is observed by a scanning electron microscope (SEM) (refer, for example, to Japanese Patent No. 2935180 and Japanese patent application publication JP-A-2002-367115). Or, a sample is thinly sliced, also by etching with a focused ion beam. Then, the sliced sample is observed by a transmission electron microscope (TEM). However, according to the method of fabricating the cross section for observation by a focused ion beam, there is a problem that relief lines are formed in the up and down direction in which the focused ion beam is emitted owing to recesses and projections at an irradiated surface of the sample. As a method of fabricating an excellent cross section for observation which resolves such a problem, for example, a method of inclining the sample to be irradiated has been proposed (refer, for example, to Japanese Patent No. 2973211). According to the method, the focused ion beam is skewed with regard to the sample, and therefore, relief lines in the up and down direction are not formed at the sample as described above, and even if there is an unfavorable effect, it would be only slight relief lines in a skewed direction, and an excellent cross section for observation can be fabricated.

However, when the sample is a thin film magnetic head and a cross section for observation is fabricated as in, for example, JP-A-2002-367115, the aspect ratio of the sample is very high, and therefore, there poses a problem that significant relief lines are formed in the direction of the focused ion beam depending on a recessed and projected shape thereof. Although it is confirmed that the method by Japanese Patent No. 2973211 reduces the relief lines, on such a sample having a high aspect ratio, an excellent cross section suitable for observation still cannot be provided, and further, the direction needs to be adjusted for inclining the sample, and therefore, there poses a problem that throughput is reduced.

The invention has been carried out in view of the above-described situation and it is an object of the invention to provide a focused ion beam apparatus capable of improving throughput and a method of fabricating/observing a cross section of a sample capable of providing an accurate observed image.

SUMMARY OF THE INVENTION

The invention proposes the following means in order to resolve the above-described problem.

A focused ion beam apparatus of the invention is characterized in comprising a sample base for mounting a sample, a three axis stage capable of moving the sample base in three directions: along two axes on a horizontal face and a vertical axis, and a first focused ion beam barrel and a second focused ion beam barrel for irradiating the sample with focused ion beams, wherein the directions of the focused ion beams of the first focused ion beam barrel and the second focused ion beam barrel are substantially opposed to each other in a plane view thereof and inclined in substantial line symmetry with regard to the vertical axis a side view thereof.

According to the focused ion beam apparatus according to the invention, the position of the sample mounted on the sample base is adjusted to be disposed at a predetermined position by the three axis stage, and the focused ion beams are emitted from the first focused ion beam barrel and the second focused ion beam barrel. The directions of the respective focused ion beams of the first focused ion beam barrel and the second focused ion beam barrel are substantially opposed to each other in the plane view, and therefore, the cross section of the sample for observation can be fabricated by simultaneously etching the cross section from both sides, and throughput in fabricating the cross section for observation can be improved. Further, the focused ion beams from the first focused ion beam barrel and the second focused ion beam barrel are inclined in substantial line symmetry with regard to the vertical axis, and therefore, relief lines are formed on the cross section for observation of the sample in skewed directions. Therefore, the relief lines can be reduced without reducing the throughput by an adjustment such as inclining the sample. At this time, the relief lines formed by the respective focused ion beams are planed off, and therefore, as a result, the relief lines are reduced, and a still more excellent cross section for observation can be fabricated. Further, when a sample for observation by a transmission electron microscope (TEM) is fabricated, the sample constituting a base member needs to be fabricated by slicing the sample, but in this way two cross section faces can also be prepared for observation simultaneously by the first focused ion beam barrel and the second focused ion beam barrel.

Further, the invention is characterized by a method of preparing/observing a cross section of a sample for observation at a predetermined position of the sample with a focused ion beam which etches the sample, and observing the cross section for observation, wherein the cross section for observation is fabricated by irradiating the sample mounted on a sample base with focused ion beams from two different irradiating directions substantially opposed to each other in a plane view thereof and inclined in substantial line symmetry with regard to the vertical axis in a side view thereof, and the cross section for observation is observed by generating secondary electrons from the cross section of the sample by irradiating the fabricated section for observation with an electron beam from a direction directed at the fabricated section for observation, and detecting the secondary electrons.

According to the method of preparing/observing a sample according to the invention, by emitting the focused ion beams from the two different directions inclined in substantial line symmetry with regard to the vertical axis in the side view, an excellent cross section for observation with reduced relief lines can be provided. Further, by irradiating the cross section for observation with the electron beam and detecting the generated secondary electron, an excellent image for observation can be provided and throughput from preparing to observing the sample can be improved.

Further, the focused ion beam apparatus preferably comprises a rotary stage capable of rotating the sample base around the vertical axis, and an inclining stage capable of rotating the sample base around axes substantially in parallel with the directions of the first focused ion beam barrel and the second focused ion beam barrel.

In the focused ion beam apparatus according to the invention, not only can the position of the sample be adjusted in the three directions of the two axes on the horizontal face and the vertical axis by the three axis stage but also the sample can be rotated around the vertical axis by the rotary stage and the inclining stage and can be rotated around axes substantially in parallel with the directions of the focused ion beams. Therefore, the cross section for observation can be fabricated by irradiating the sample with the focused ion beam at various angles.

Further, in the focused ion beam apparatus, it is preferable that the respective directions of the focused ion beams of the first focused ion beam barrel and the second focused ion beam barrel have an angle of inclination no less than 20 degrees and no more than 70 degrees relative to the vertical axis.

In the focused ion beam apparatus according to the invention, by making the respective directions of the focused ion beams of the first focused ion beam barrel and the second focused ion beam barrel no less than 20 degrees and no more than 70 degrees relative to the vertical axis, the sample can be irradiated with the focused ion beams without the focused ion beams interfering with each other and also with the sample.

Further, in the focused ion beam apparatus, it is preferable that a first electron beam barrel for irradiating the sample with an electron beam, and a first secondary electron detector for detecting secondary electrons generated from the sample upon irradiation with the electron beam from the first electron beam barrel be arranged so that the direction of the electron beam from the first electron beam barrel is substantially orthogonal to the direction of the focused ion beams of the first focused ion beam barrel and the second focused ion beam barrel in a plane view thereof.

According to the focused ion beam apparatus according to the invention, the cross section for observation can be observed by emitting the electron beam from the first focused ion beam barrel set facing the fabricated section for observation, and detecting the secondary electrons generated from the cross section for observation of the sample by the secondary electron detector. For that arrangement, since the direction of the electron beam emitted from the first electron beam barrel is substantially orthogonal to the respective directions of the focused ion beams of the first focused ion beam barrel and the second focused ion beam barrel, the cross section for observation can be observed after fabricating the cross section for observation with the first focused ion beam barrel and the second focused ion beam barrel without changing the direction of the sample. Therefore, throughput from preparing to observing the sample can be further improved.

Further, in the focused ion beam apparatus, it is preferable that a second electron beam barrel for irradiating the sample with an electron beam in the opposite direction to the electron beam of the first electron beam barrel in a plane view thereof, and a second secondary electron detector for detecting secondary electrons generated from the sample by irradiation with the electron beam from the second electron beam barrel be provided.

Further, in the method of preparing/observing a cross section of a sample, it is further preferable that the electron beams are emitted from two directions substantially opposed to each other in a plane view thereof in correspondence with the focused ion beams emitted from two different directions, and the respective secondary electrons generated by each of the electron beams are detected.

According to the focused ion beam apparatus and the method of preparing/observing a cross section of a sample according to the invention, one face can be observed by irradiation with the electron beam from the first electron beam barrel and detecting the secondary electrons with the first secondary electron detector, while at the same time, the other face on the opposite side can also be observed by irradiation with the electron beam from the second electron beam barrel and detecting the secondary electrons with the second secondary electron detector. That is, for example, in fabricating the sample for observation of a transmission electron microscope, the two observed faces of the sample for observation are simultaneously prepared by the focused ion beams emitted from the first focused ion beam barrel and the second focused ion beam barrel in the two different directions. Further, the two faces of the sample for observation can be simultaneously observed by detecting the generated secondary electrons with the first secondary electron detector and the second secondary electron detector when the electron beams from the first electron beam barrel and the second electron beam barrel in the two directions irradiate the two faces of the sample for observation, without changing the direction of the sample for observation. Therefore, the throughput from preparing to observing the sample can further be improved.

Further, in the focused ion beam apparatus, it is preferable to provide a first gas gun and a second gas gun operating in correspondence with respective beams of the first focused ion beam barrel and the second focused ion beam barrel so as to inject deposition gasses simultaneously with emission of the focused ion beams.

Further, in the method of preparing/observing a cross section of a sample, it is preferable that a deposition is carried out on a surface of the sample by injecting a deposition gas in correspondence with the focused ion beams from the two different irradiating directions so as to inject deposition gas at the same time as the respective focused ion beams as a step preceding etching the sample by the focused ion beams.

According to the focused ion beam apparatus and the method of preparing/observing a cross section of a sample according to the invention, the deposition can be carried out simultaneously at both sides of the sample by emitting the focused ion beams from the first focused ion beam barrel and the second focused ion beam barrel and injecting the deposition gasses from the first gas gun and the second gas gun so that films can be formed on both surfaces of the sample. Therefore, even a sample having a high aspect ratio can be given films uniformly without inclining the sample, and throughput in disposition can be improved. Further, in fabricating the cross section for observation of the sample, by forming the uniform film on the surface of the sample before etching the sample with the focused ion beams, relief lines owing to recesses and the projections of the sample can be reduced, and a more excellent cross section for observation can be fabricated.

Further, in the focused ion beam apparatus, it is preferable to provide an argon ion beam barrel for irradiating the sample with an argon ion beam along the direction of the vertical axis.

Further, in the method of preparing/observing a cross section of a sample, it is preferable that the cross section for observation is fabricated with the focused ion beams, after which finishing preparation of the cross section for observation is carried out by irradiating the cross section for observation with an argon ion beam, and thereafter, the cross section is observed.

According to the focused ion beam apparatus and the method of preparing/observing a cross section of a sample according to the invention, after fabricating the cross section for observation with the focused ion beams emitted from the first focused ion beam barrel and the second focused ion beam barrel in the two different directions, finishing preparation of the cross section for observation can be done by irradiating the cross section for observation with the argon beam from the argon beam barrel, and therefore, a still more excellent cross section for observation can be fabricated.

Further, in the focused ion beam apparatus, there may be constructed a constitution further comprising an optical microscope capable of optically observing the sample from the direction of the vertical axis.

In the focused ion beam apparatus according to the invention, by providing the optical microscope, the sample can be prepared while optically observing the fabricated cross section for observation. Therefore, the sample can be more accurately prepared.

Further, in the method of preparing/observing a cross section of a sample, a constitution is preferable in which the length of the cross section for observation is measured by irradiating the sample with the electron beam, acquiring an image of the cross section for observation by detecting the secondary electrons generated from the sample, discriminating two predetermined boundary lines by the color tone difference of the observed image, and measuring the distance between the boundary lines.

According to the method of preparing/observing a cross section according to the invention, even though the relief lines of the cross section for observation are reduced as the cross section is formed, there still are relief lines in skewed directions. Therefore, the boundary lines of the cross section whose length is to be measured can easily and accurately be discriminated by the color tone difference of the observed image and the length of the cross section can accurately be measured.

According to the focused ion beam apparatus and the method of preparing/observing the cross section of the sample of the invention, by irradiating the sample with the focused ion beams from two different directions opposed to each other in the plane view and oblique to the vertical axis, the relief lines formed on the cross section for observation can be reduced. Therefore, the excellent cross section for observation can be fabricated and observed. Further, by emitting the focused ion beams simultaneously from the two different directions, also the throughput in fabricating the cross section for observation can simultaneously be improved.

DETAILED DESCRIPTION OF THE PREFERRED EMBODIMENT

First Embodiment

Figure 1:
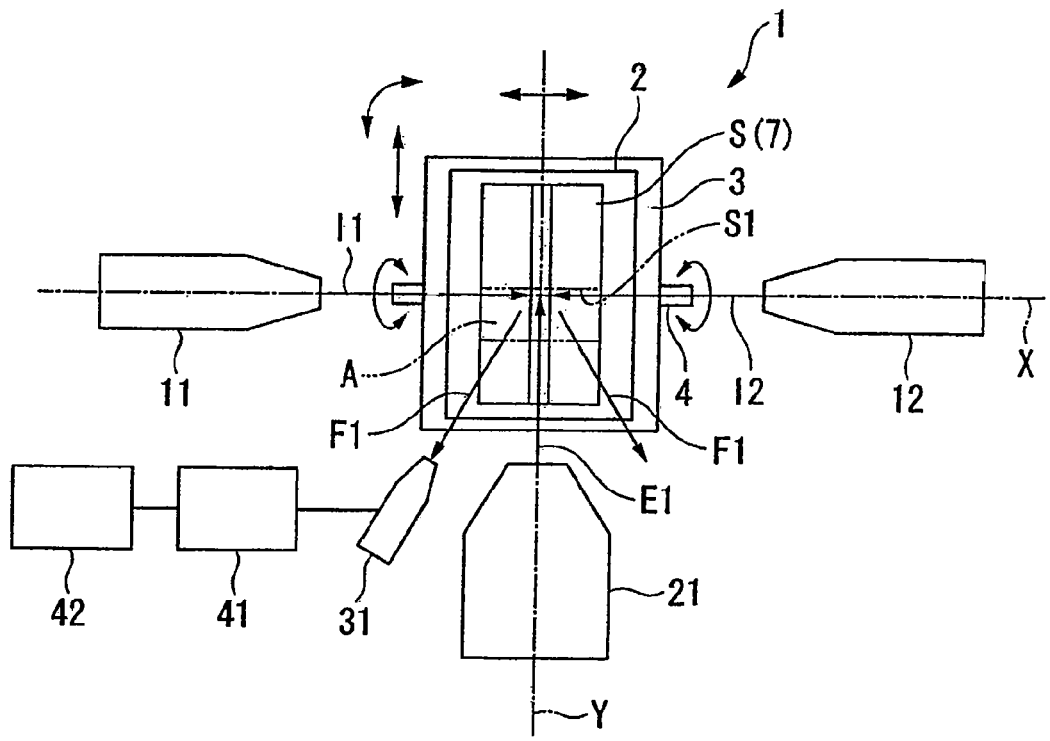
FIG. 1 is an outline view viewing a focused ion beam apparatus according to a first embodiment of the invention by a plane view.
Figure 2:
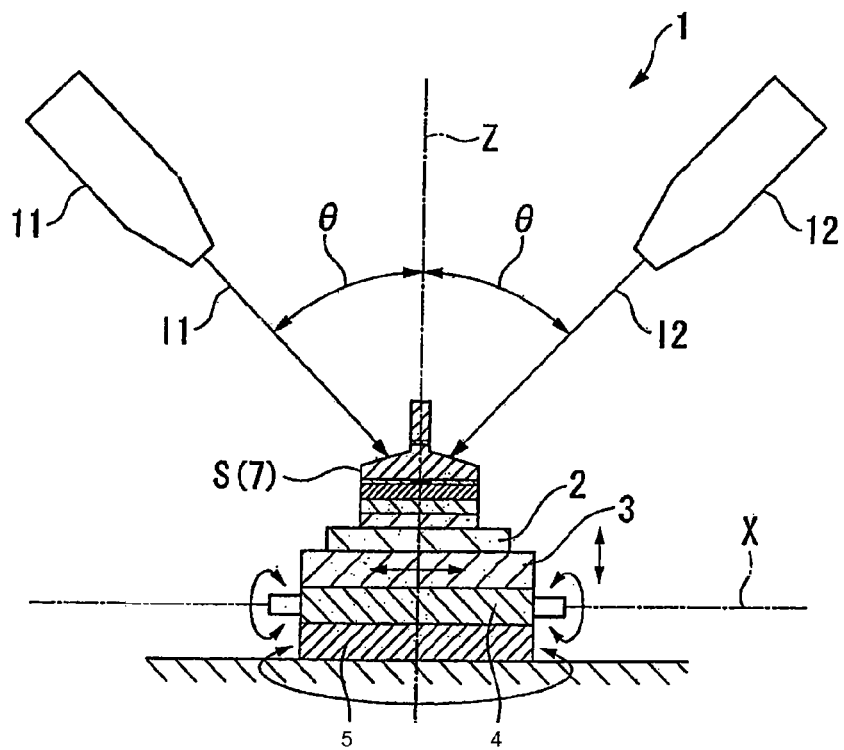
FIG. 2 is an outline view viewing the focused ion beam apparatus of the first embodiment of the invention by a side view.
Figure 3:
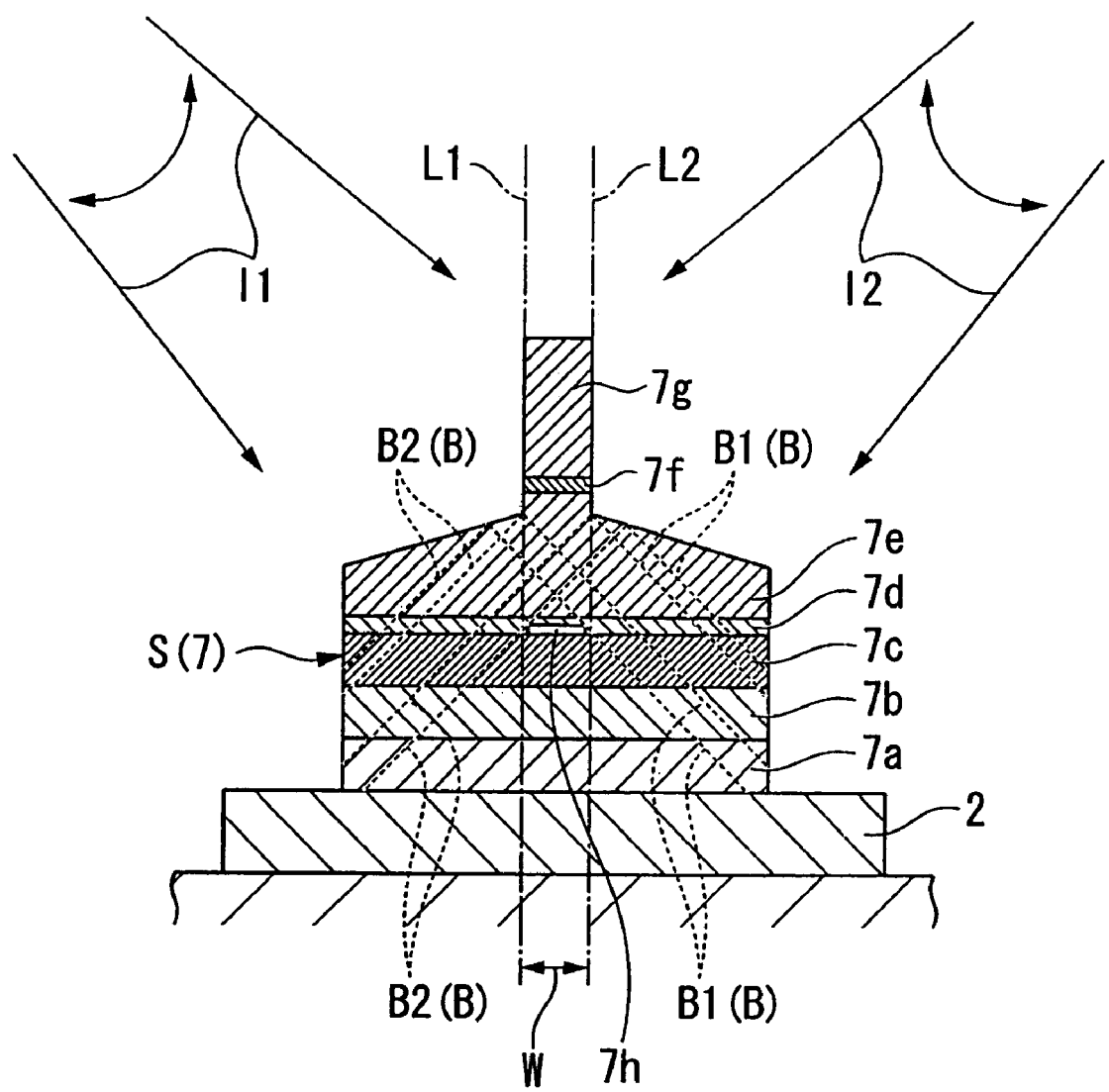
FIG. 3 is an explanatory view of the focused ion beam apparatus of the first embodiment of the invention.

FIG. 1 through FIG. 3 show a first embodiment according to the invention. As shown by FIG. 1, a focused ion beam apparatus 1 includes a sample base 2 for mounting a sample S, and a first focused ion beam barrel 11 and a second focused ion beam barrel 12 respectively capable of emitting focused ion beams I1, I2 to the sample S mounted on the sample base 2. Both of the first focused ion beam barrel 11 and the second focused ion beam barrel 12 have ion sources of gallium ions or the like (not illustrated) inside, and are capable of emitting the focused ion beams I1, I2 by drawing out and accelerating the ion beams by applying voltages, and focusing the ion beams with electrostatic lenses (not illustrated). Further, the first focused ion beam barrel 11 and the second focused ion beam barrel 12 have deflecting electrodes (not illustrated) inside, and are capable of emitting ion beams deflected over a predetermined range by the deflecting electrodes. In addition, publicly known features such as a variable diaphragm or a blanking electrode may be included.

As shown by FIG. 1, the first focused ion beam barrel 11 and the second focused ion beam barrel 12 are arranged such that the directions of the focused ion beams I1, I2 emitted respectively therefrom are substantially opposed to each other in a plane view thereof and are inclined in substantial line symmetry with regard to the vertical Z axis in a side view thereof. Further, the directions of, the focused ion beam I1 of the first focused ion beam barrel 11 and of the focused ion beam I2 of the second focused ion beam barrel 12 are set such that their angles θ of inclination relative to the vertical axis are no less than 20 degrees and equal to and no more than 70 degrees. Thereby, the first focused ion beam barrel 11 and the second focused ion beam barrel 12 can irradiate the sample S with the focused ion beams I1, I2 without interfering with each other and without interfering also with the sample S.

Further, as shown by FIG. 1, the focused ion beam apparatus 1 includes an electron beam barrel 21 for irradiating the sample S with an electron beam E1, and a secondary electron detector 31 for detecting secondary electrons F1 generated from the sample S. The electron beam barrel 21 includes an electron source, not illustrated, inside it, and is capable of generating the electron beam E1, drawing out and accelerating an electron beam by applying a voltage and focusing the electron beam by an electromagnetic lens, not illustrated. Further, the electron beam barrel 21 includes a deflecting electrode, not illustrated, inside it, and is capable of irradiating a predetermined target range by deflecting the electron beam with the deflecting electrode. In addition, a well-known feature such as a variable diaphragm or a blanking electrode may be included. The electron beam barrel 21 is arranged such that the direction of the electron beam E1 is substantially orthogonal to the directions of the focused ion beams I1, I2 emitted respectively from the first focused ion beam barrel 11 and the second focused ion beam barrel 12, in a plane view thereof. Further, by scanning the electron beam E1 at an observed portion of the sample S, a distribution of intensity of the secondary electrons F1 detected by the secondary electron detector 31 is formed into an image by an image processing portion 41 and displayed on a display portion 42 as a brightness modulated image. Further, in the image processing portion 41, a result of detecting the secondary electrons F1 can be formed into the image, a boundary can be discriminated from a color tone difference thereof, and the distance between specific points can be measured.

Further, as shown by FIG. 1 and FIG. 2, the focused ion beam apparatus 1 includes a three axis stage 3 capable of moving the sample base 2 in three directions: along the X axis and Y axis constituting two axes on water level as well as the Z axis constituting a vertical axis. Here, the X axis is the axis substantially coinciding with the directions of the focused ion beams I1, I2 of the first focused ion beam barrel 11 and the second focused ion beam barrel 12 in a plane view thereof, and Y axis is an axis substantially coinciding with a direction of the electron beam E1 of the electron beam barrel 21 in plane view thereof. Further, the focused ion beam apparatus 1 further includes an inclining stage 4 capable of rotating the sample base 2 along the X axis, and a rotary stage 5 capable of rotating the sample base 2 around the Z axis.

Next, operation of the focused ion beam apparatus 1 and a method of preparing/observing a cross section of a sample using the focused ion beam apparatus 1 will be explained. As shown by FIG. 1 and FIG. 2, according to the embodiment, a thin film magnetic head 7 is formed on a wafer as the sample S. As shown by FIG. 3, the thin film magnetic head 7 is provided with a laminated layer structure of a substrate 7a, a substrate ground 7b, a lower shield film 7c, an insulating layer 7d, a first magnetic layer 7e, a gap layer 7f and a second magnetic layer 7g, and an MR element 7h is embedded in the insulating layer 7d. An explanation will be given of the example in this embodiment of inspecting the laminated layer structure and the configuration of a cross section by fabricating and observing a cross section S1 for observation, preparing a cross section by irradiating a range A of the thin film magnetic head 7 constituting the sample S with the focused ion beam.

As shown by FIG. 1 and FIG. 2, first, the position and direction of the sample S are adjusted such that the range A of the sample S can be irradiated with the focused ion beams I1, I2, by driving the three axis stage 3, the inclining stage 4, and the rotary stage 5. Further, the focused ion beams I1, I2 are emitted from the first focused ion beam barrel 11 and the second focused ion beam barrel 12. Etching is carried out in the range A of the sample S by moving the respective focused scanning ion beams I1, I2 by deflecting electrodes (not illustrated) as necessary and moving the three axis stage 3 along the Y axis. As described above, directions of the respective focused ion beams I1, I2 of the first focused ion beam barrel 11 and the second focused ion beam barrel 12 are substantially opposed to each other in the plane view. Therefore, the cross section S1 for observation can be fabricated by etching the sample S simultaneously from both sides by the first focused ion beam barrel 11 and the second focused ion beam barrel 12, and throughput in fabricating the cross section S1 for observation can be improved. Further, as shown by FIG. 3, the focused ion beams I1, I2 are oblique to the vertical Z axis. Therefore, although relief lines B (B1, B2) are formed owing to recesses and projections or the like of the surface of the sample S, the directions of these lines can be skewed in directions coinciding with the different directions of the focused ion beams I1, I2. That is, the relief line B can be reduced without the reduction throughput that would be caused by an adjustment of inclination of the sample S or the like. Further, at that occasion, the focused ion beams I1, I2 shave off the relief lines B1, B2 respectively formed thereby, and therefore, as a result, the excellent cross section S1 for observation can be fabricated with reduced relief lines B. Further, not only the position of the sample S can be adjusted in three directions of X axis, Y axis and Z axis by the three axis stage 3 but also the sample S can be inclined with regard to the X axis or can be rotated around the X axis. Therefore, the cross section S1 for observation can be fabricated by irradiating the sample S with the focused ion beams I1, I2 from various angles.

Next, the fabricated cross section S1 for observation is observed. That is, as shown by FIG. 1, the cross section S1 for observation is irradiated by the electron beam E1 from the electron beam barrel 21. Further, the secondary electrons F1 generated from the cross section S1 for observation by scanning the cross section S1 for observation with the electron beams E1 moved by a deflecting electrode, not illustrated, are detected by the secondary electron detector 31. Further, based on a result of the detection, the intensity distribution of the secondary electrons F1 can be formed into an image by the image processing portion 41 and the created image of the cross section S1 can be displayed on the display portion 42. At that occasion, the excellent cross section S1 for observation having small relief lines B can be fabricated by the first focused ion beam barrel 11 and the second focused ion beam barrel 12, and therefore, a clear and accurate observed image can be provided. Further, the direction of the electron beam E1 from the electron beam barrel 21 is substantially orthogonal to the directions of the focused ion beams I1, I2 from the first focused ion beam barrel 11 and the second focused ion beam barrel 12 in a plane view, and therefore, the cross section S1 for observation can be observed by irradiation with the electron beam E1 from a position facing the cross section S1 for observation without changing the direction of the sample S after fabricating the cross section S1 for observation. Therefore, throughput from preparation to observation of the sample S can be improved.

Next, an example of measuring a width W of the second magnetic layer 7g of the sample S utilizing the observed image provided by the first focused ion beam apparatus 1 as shown by FIG. 3 will be explained. First, the image processing portion 41 constructs a brightness modulated image based on the result of detection of the secondary electrons F1 inputted from the secondary electron detector 31. Further, two boundary lines L1, L2 in the width W direction of the first magnetic layer 7e are discriminated in accordance with an instruction by an operating portion, not illustrated. More specifically, the discrimination is carried out based on a color tone difference of the provided image. At that occasion, as described above, the observed image of the excellent cross section S1 for observation having small relief lines B can be provided, and also the formed relief lines B are in skewed directions relative to the boundary lines L1, L2 constituting the object of measurement, and therefore, the discrimination of the boundary lines L1, L2 is easy, and a length of the cross section can be measured accurately.

Although described above, the focused ion beam apparatus 1 can simultaneously emit the focused ion beams I1, I2 which are inclined to the vertical axis from two different directions substantially opposed to each other in the plane view, and therefore, an excellent cross section for observation having small relief lines can efficiently be fabricated without inclining or inverting the sample S. Further, the electron beam E1 can be orthogonal to the focused ion beams I1, I2 in the plane view, and therefore, the fabricated cross section S1 for observation can be observed without adjusting the position and the direction of the cross section S1 for observation. Therefore, the throughput from fabricating to observing the cross section for observation can also be improved.

Second Embodiment

Figure 4:
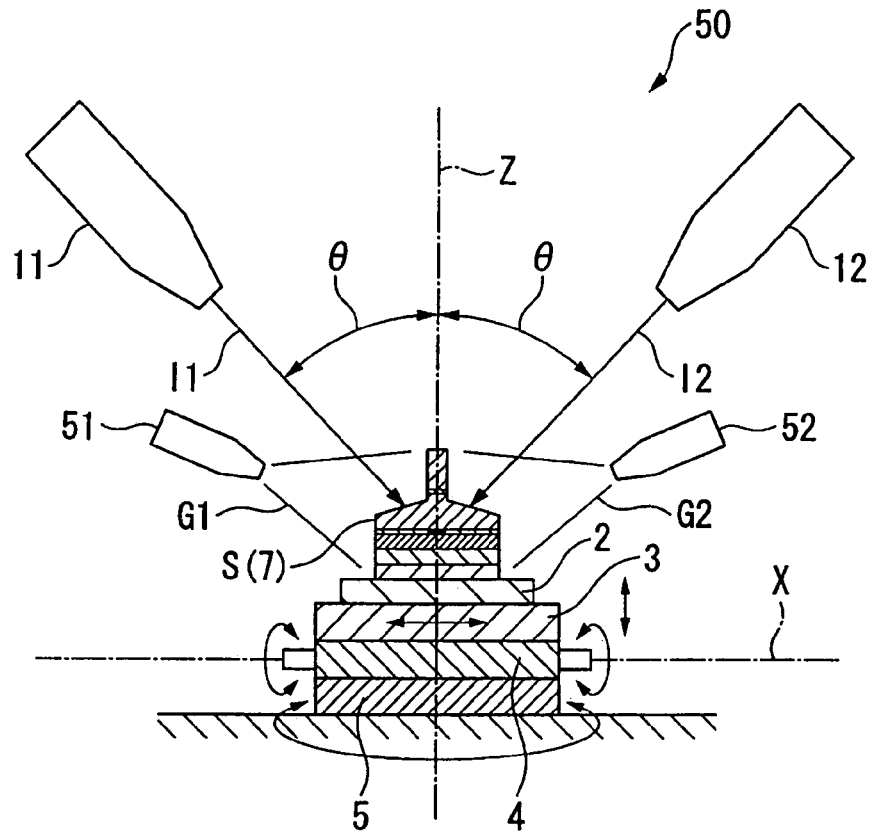
FIG. 4 is an outline view viewing a focused ion beam apparatus of a second embodiment of the invention by a side view.
Figure 5:
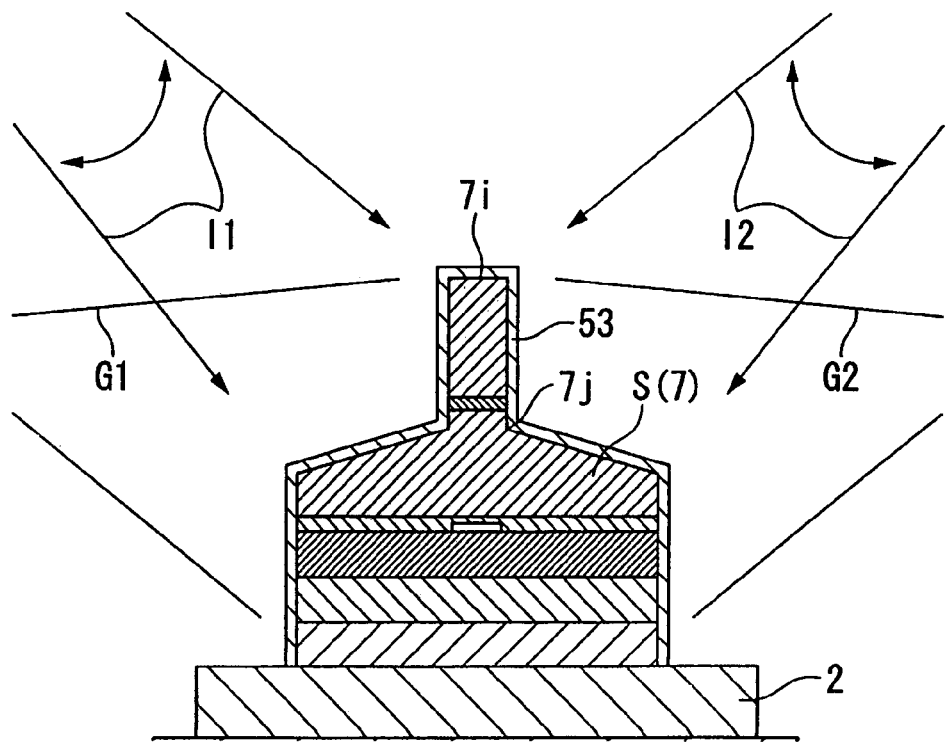
FIG. 5 is an explanatory view of the focused ion beam apparatus of the second embodiment of the invention.

FIG. 4 and FIG. 5 show a second embodiment according to the invention. In the embodiment, members in common with the above-described embodiment are given the same notations and explanations thereof will be omitted.

As shown by FIG. 4, a focused ion beam apparatus 50 of the embodiment includes a first gas gun 51 and a second gas gun 52 for simultaneously injecting deposition gasses G1, G2 respectively in correspondence with the first focused ion beam barrel 11 and the second focused ion beam barrel 12. Here, the deposition gasses G1, G2 are, for example, W (CO) 6. By injecting the deposition gasses to the sample S along with irradiation by the focused ion beams I1, I2, a film 53 of tungsten can be formed on the surface of the sample S. Further, the deposition gasses G1, G2 are not limited to those described above, but can be selected appropriately in accordance with the material of the film 53.

According to the focused ion beam apparatus 50, the film can be formed on both sides of the surface of the sample S simultaneously by irradiation with the focused ion beams I1, I2 from the first focused ion beam barrel 11 and the second focused ion beam barrel 12 and injecting the deposition gasses G1, G2 from the first gas gun 51 and the second gas gun 52. In the case of the sample S having a high aspect ratio as in the thin film magnetic head 7, when the deposition is carried out from an upper side, the upper portion film 7i formed first forms a shadow, and a film is not formed uniformly on the base portion 7j. However, with this invention, the film can be formed simultaneously and uniformly on both sides, restraining the above-described phenomenon by injecting the focused ion beams I1, I2 obliquely to the Z axis, and further, injecting the deposition gasses G1, G2. Further, since the deposition can be carried out simultaneously from both sides, throughput of the deposition can be improved since it is not necessary to incline or invert the sample. Further, the relief lines B owing to recesses and projections of the sample S can be reduced, and a more excellent cross section S1 for observation can be fabricated, by forming the film 53 on the surface of the sample S uniformly as a step preceding etching the sample S by the focused ion beams I1, I2.

Third Embodiment

Figure 6:
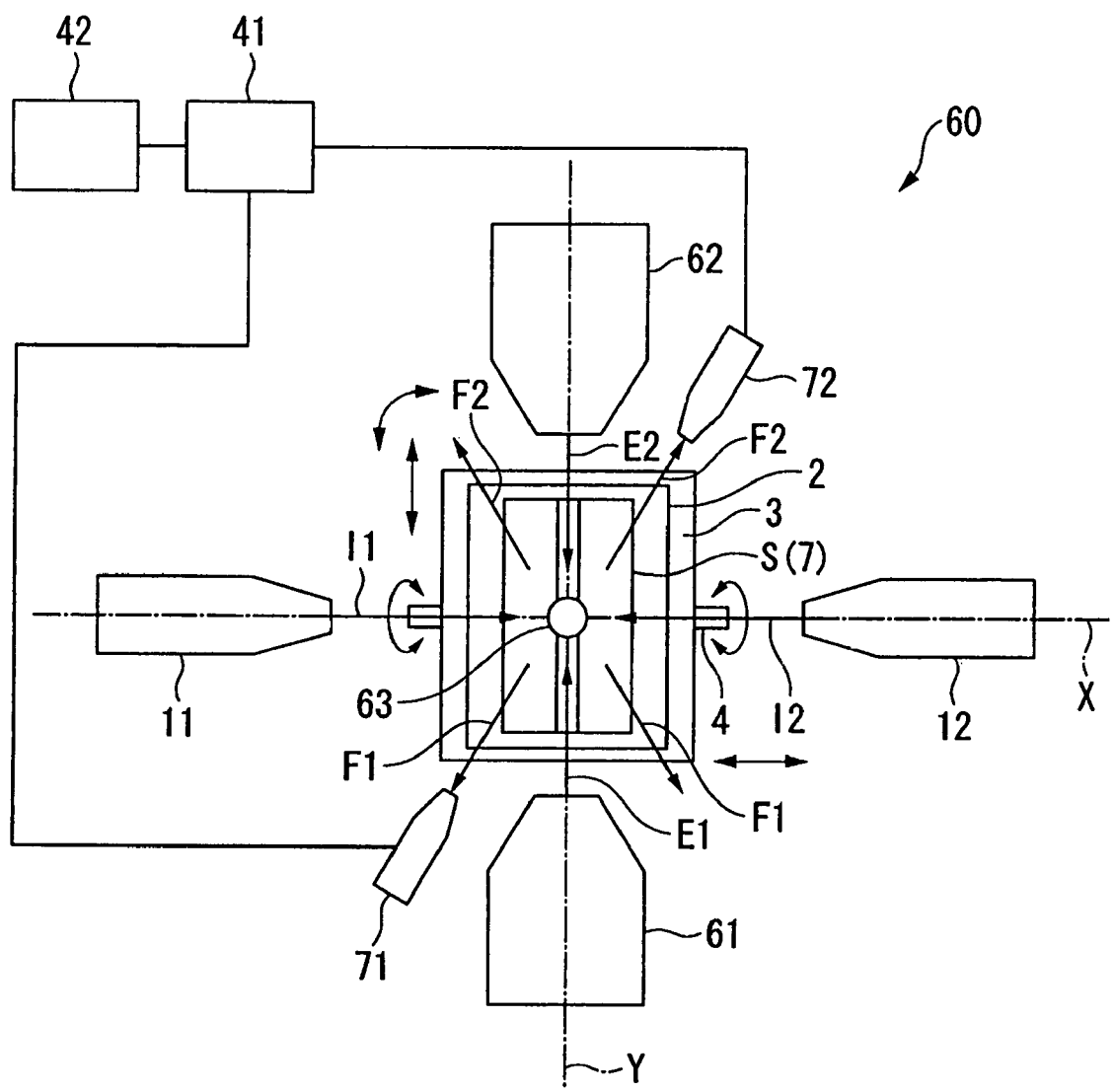
FIG. 6 is an outline view viewing a focused ion beam apparatus of a third embodiment of the invention by a plane view.
Figure 7:
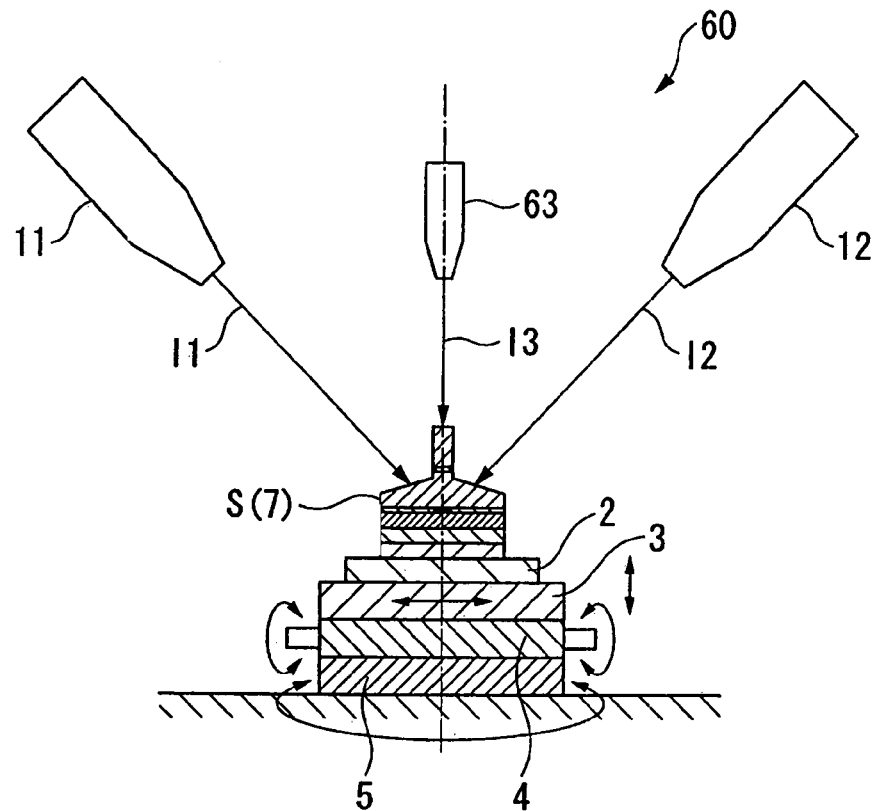
FIG. 7 is an outline view viewing the focused ion beam apparatus of the third embodiment of the invention by a side view.
Figure 8:
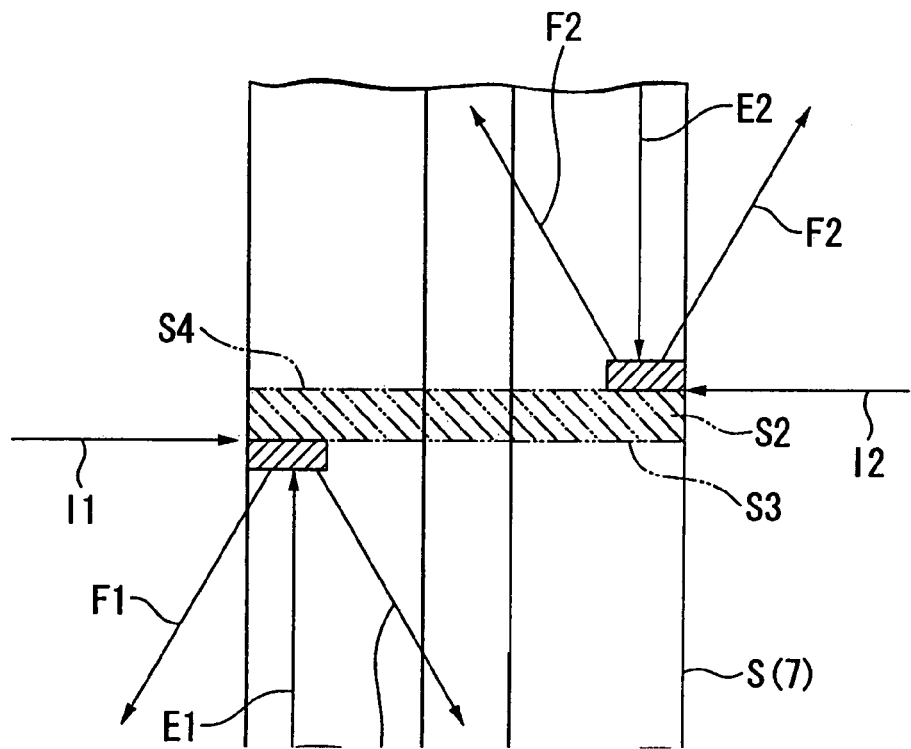
FIG. 8 is an explanatory view of the focused ion beam apparatus of the third embodiment of the invention.

FIG. 6 through FIG. 8 show a third embodiment according to the invention. In the embodiment, members common to members used in the above-described embodiments are attached with the same notations and an explanation thereof will be omitted.

As shown by FIG. 6 and FIG. 7, a focused ion beam apparatus 60 of the embodiment includes a first electron beam barrel 61 and a second electron beam barrel 62 for irradiating the sample S with electron beams E1, E2, and a first secondary electron detector 71 and a second secondary electron detector 72 for respectively detecting secondary electrons F1, F2 generated from the sample S by irradiating the sample S with the electron beams E1, E2. The first electron beam barrel 61 and the second electron beam barrel 62 are arranged such that the directions of the respective electron beams E1, E2 are substantially opposed to each other in a plane view thereof, and substantially orthogonal to the focused ion beams I1, I2 respectively emitted from the first focused ion beam barrel 11 and the second focused ion beam barrel 12, in the plane view. Further, respective intensity distributions of the secondary electrons F1, F2 detected by the first secondary electron detector 71 and the second secondary electron detector 72 are formed into images by the image processing portion 41 and separately displayed on the display portion 42. Further, the focused ion beam apparatus 60 further includes an argon ion beam barrel 63 capable of irradiating the sample S with an argon ion beam I3 in the direction of the Z axis. Whereas the first focused ion beam barrel 11 and the second focused ion beam barrel 12 generate the focused ion beams I1, I2 with an acceleration voltage of about 5 kV to 30 kV, the argon ion beam barrel 63 can generate the argon ion beam I3 with a low energy of about 0.5 kV to 15 kV.

Next, operation of the focused ion beam apparatus 60 will be explained by taking the example of fabricating a sample for observation for a transmission electron microscope (TEM) from the sample S which is a thin film magnetic head 7. In a transmission electron microscope, in order to observe a sample for observation by transmitting an electron beam therethrough, it is necessary to fabricate a sample for observation from the original sample S by slicing the sample to a thickness through which the electron beam can be transmitted. As shown by FIG. 8, first, the focused ion beams I1, I2 irradiate both sides of the sample S from the first focused ion beam barrel 11 and the second focused ion beam barrel 12. At that time, the focused ion beam I1 of the first focused ion beam barrel 11 irradiates a portion of one face S3 of a sample S2 for observation and the focused ion beam I2 of the second focused ion beam barrel 12 irradiates a portion of the other face S4, after finely adjusting the directions of focused ion beams I1, I2 with deflecting electrodes, not illustrated. In this way, the two faces S3, S4 of the sample S2 to be observed can simultaneously be prepared by the first focused ion beam barrel 11 and the second focused ion beam barrel 12, and throughput in fabricating the sample S2 for observation can be improved. Further, the two faces S3, S4 of the prepared sample S2 to be observed can be fabricated by the first electron beam barrel 61 and the second electron beam barrel 62 without changing the direction of the sample S. Therefore, throughput from preparing to observing the sample S can further be improved. Further, in a step preceding observation, the two observed faces S3, S4 of the sample S2 for observation fabricated by the first focused ion beam barrel 11 and the second focused ion beam barrel 12 can be given finishing preparation by irradiation with the argon ion beam from the argon ion beam barrel 63. Therefore, the observed faces S3, S4 can be made to be still more excellent.

Fourth Embodiment

Figure 9:
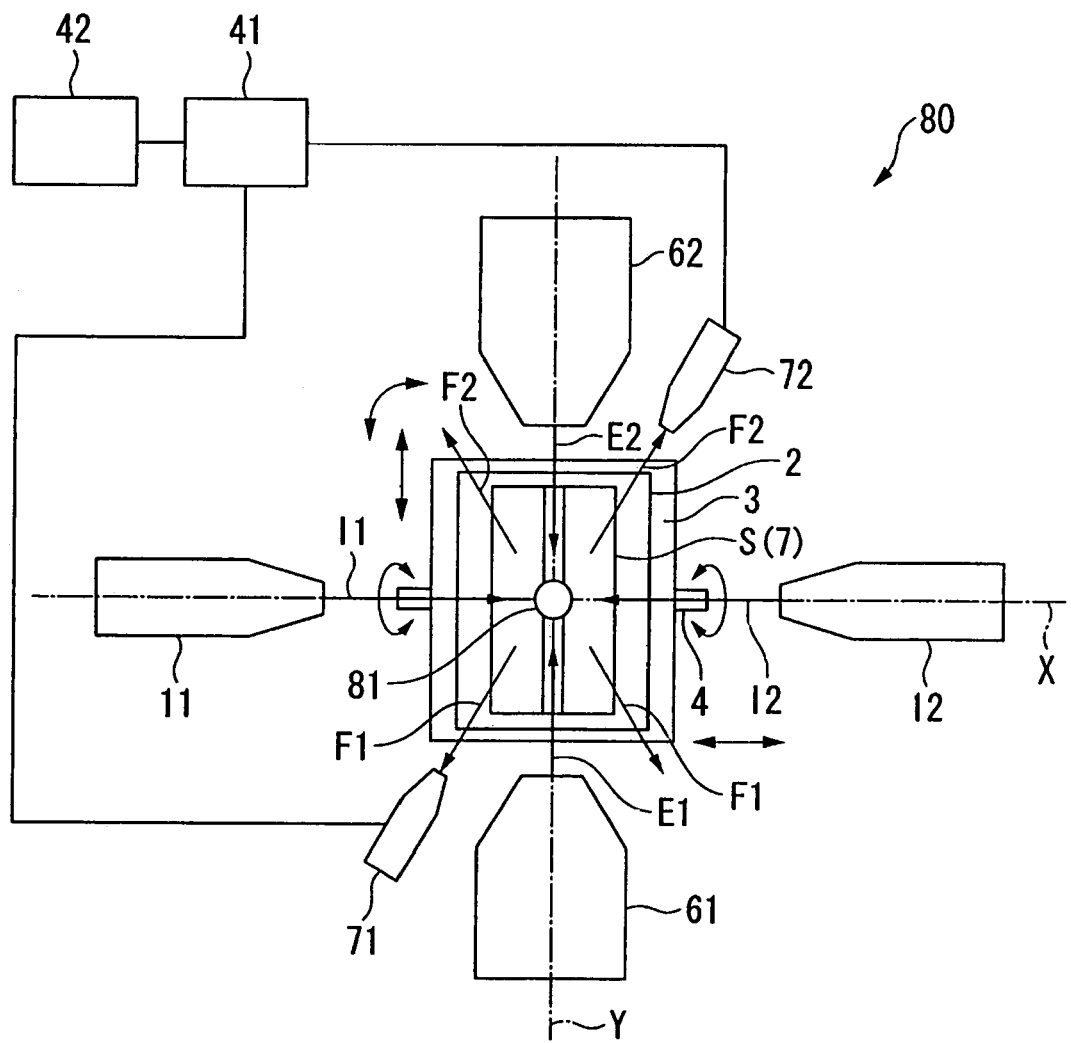
FIG. 9 is an outline view viewing a focused ion beam apparatus of a fourth embodiment of the invention by a plane view.
Figure 10:
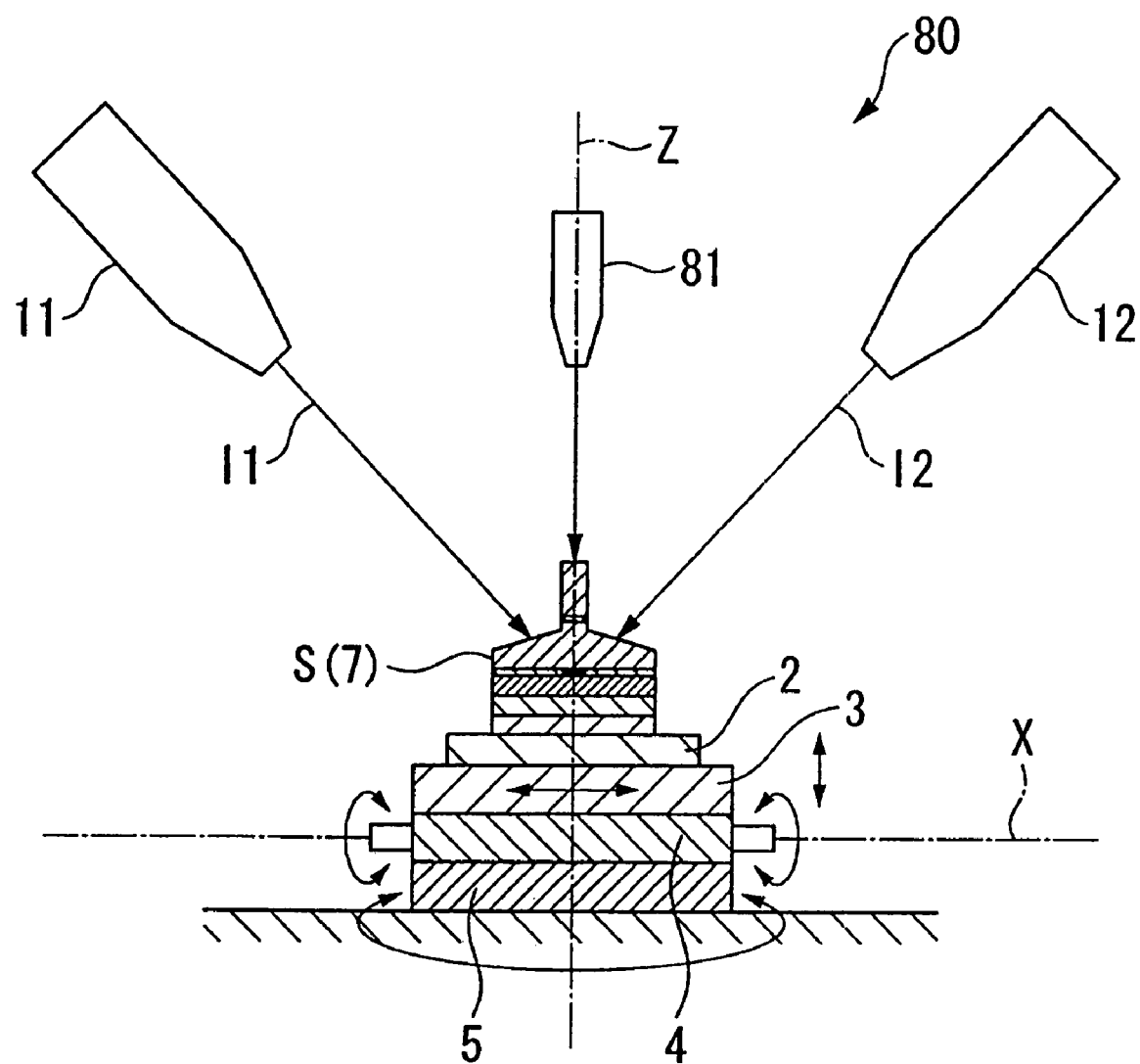
FIG. 10 is an outline view viewing the focused ion beam apparatus of the fourth embodiment of the invention by a side view.

FIG. 9 and FIG. 10 show a fourth embodiment according to the invention. In the embodiment, members in common with the above-described embodiments are given the same notations, and explanation thereof will be omitted. A focused ion beam apparatus 80 according to this embodiment includes an optical microscope 81 capable of optically observing the sample S from the direction of Z axis. According to the focused ion beam apparatus 80, the sample S can efficiently be fabricated, the sample S can optically be observed, and therefore, the sample S can be more accurately prepared.

Although embodiments of the invention have been described in details in reference to the drawings, specific constitutions are not limited to the embodiments but also may include changes in design or the like within the range not deviating from the gist of the invention.

Further, although according to the respective embodiments, the position and the direction of the sample S can be adjusted by the three axis stage 3, the inclining stage 4, and the rotary stage 5, even if only the three axis stage 3 is provided, an excellent cross section for observation having small the relief lines can be fabricated. Further, although according to the respective embodiments, the fabricated cross section for observation, or the two faces S3, S4 of the sample S2 to be observed, are irradiated with an electron beam, the secondary electrons are detected, and an observed image is provided by detecting secondary electrons, alternatively secondary electrons or secondary ions generated from the sample S when irradiated by the focused ion beams I1, I2 from the first focused ion beam barrel 11 and the second focused ion beam barrel 12 may be detected and an image may be formed therefrom.

What is claimed is:

1. A focused ion beam apparatus comprising:
    a sample base for mounting a sample;
    a three axis stage capable of moving the sample base in three directions: along two axes on a horizontal face and along a vertical axis;
    a first focused ion beam barrel and a second focused ion beam barrel for irradiating the sample with focused ion beams; and
    a first electron beam barrel for irradiating the sample with an electron beam;
    wherein the irradiating directions of the focused ion beams of the first focused ion beam barrel and the second focused ion beam barrel are substantially opposed to each other in a planar view and inclined in substantial line symmetry with regard to the vertical axis in a side view; and
    wherein the first electron beam barrel is arranged such that the direction of the electron beam is substantially orthogonal to the respective directions of the focused ion beams of the first focused ion beam barrel and the second focused ion beam barrel in the planar view thereof.

2. The focused ion beam apparatus according to claim 1, further comprising:
    a rotary stage capable of rotating the sample base around the vertical axis; and
    an inclining stage capable of rotating the sample base around axes substantially in parallel with the irradiating directions of the first focused ion beam barrel and the second focused ion beam barrel.

3. The focused ion beam apparatus according to claim 1, wherein both of the respective directions of irradiating the focused ion beams of the first focused ion beam barrel and the second focused ion beam barrel have an angle of inclination no less than 20 degrees and equal to and no greater than 70 degrees relative to the vertical axis.

4. The focused ion beam apparatus according to claim 1, wherein further comprising:
    a first secondary electron detector for detecting a secondary electron generated from the sample by irradiating the sample with the electron beam from the first electron beam barrel.

5. The focused ion beam apparatus according to claim 4, further comprising:
    a second electron beam barrel for irradiating the sample with an electron beam in the opposite direction of the electron beam of the first electron beam barrel in a plane view thereof; and
    a second secondary electron detector for detecting secondary electrons generated from the sample when irradiated with the electron beam from the second electron beam barrel.

6. The focused ion beam apparatus according to claim 1, further comprising:
    a first gas gun and a second gas gun operated in correspondence with the first focused ion beam barrel and the second focused ion beam barrel so as to inject deposition gasses at the same time as irradiation with the focused ion beams.

7. The focused ion beam apparatus according to claim 1, further comprising:
    an argon ion beam barrel for emitting an argon ion beam in the direction of the vertical axis to the sample.

8. The focused ion beam apparatus according to claim 1, further comprising:
    an optical microscope capable of optically observing the sample from the direction of the vertical axis.

9. A method of preparing/observing a cross section of a sample, fabricating a cross section for observation at a predetermined position of the sample by irradiating a focused ion beam to etch the sample and observing the cross section;
    wherein the cross section for observation is fabricated by irradiating the sample with focused ion beams mounted on a sample base from two different irradiating directions substantially opposed to each other in a plane view thereof and inclined in substantial line symmetry with regard to the vertical axis in a side view thereof; and
    wherein the cross section for observation is observed by generating secondary electrons from the cross section for observation of the sample by irradiating the fabricated section with an electron beam directed from a direction substantially orthogonal to the plane view for observation from a direction facing the fabricated section, and detecting the secondary electrons.

10. The method of preparing/observing a cross section of a sample according to claim 9, wherein a deposition is carried out on a surface of the sample in correspondence with the respective focused ion beams by injecting a deposition gas at the same time that the focused ion beams are emitted from the two different irradiating directions as a step preceding etching the sample by the focused ion beams.

11. The method of preparing/observing a cross section of a sample according to claim 9, wherein the cross section for observation is fabricated by the focused ion beams, after which finishing preparation of the cross section for observation is done by irradiating it with an argon ion beam, and then the cross section is observed.

12. The method of preparing/observing a cross section of a sample according to claim 9, wherein the length of the cross section for observation is measured by irradiating the sample with the electron beam, wherein an observed image of the cross section for observation is acquired by detecting the secondary electrons generated from the sample, discriminating two predetermined boundary lines by the color tone difference of the observed image and measuring a distance between the boundary lines.

13. The method of preparing/observing a cross section of a sample according to claim 9, wherein generating secondary electrons from the cross section for observation of the sample comprises irradiating the fabricated section with two electron beams.

14. The method of preparing/observing a cross section of a sample according to claim 13, wherein the electron beams are emitted from two irradiating directions substantially opposed to each other in a plane view thereof in correspondence with the focused ion beams emitted from two different irradiating directions, and the secondary electron beams generated upon irradiation by the respective electron beams are respectively detected.

* * * * *